US00PP30362P3

(12) United States Plant Patent
Stemkens

(10) Patent No.: US PP30,362 P3
(45) Date of Patent: Apr. 9, 2019

(54) ***ARENARIA* PLANT NAMED 'AMOZ0002'**

(50) Latin Name: *Arenaria montana*
Varietal Denomination: AMOZ0002

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/732,165

(22) Filed: Sep. 27, 2017

(65) Prior Publication Data

US 2019/0045694 P1 Feb. 7, 2019

(30) Foreign Application Priority Data

Aug. 1, 2017 (EM) ..... 2017/1899

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new *Arenaria* plant named 'AMOZ0002' particularly distinguished by the medium sized white flower and very compact plant habit that does not need cold temperatures to flower.

1 Drawing Sheet

Latin name of the genus and species of the plant claimed: *Arenaria montana.*

Varietal denomination: 'AMOZ0002'.

BACKGROUND OF THE NEW PLANT

The present invention comprises a new *Arenaria*, botanically known as *Arenaria montana*, and hereinafter referred to by the variety name 'AMOZ0002'.

'AMOZ0002' is a product of a planned breeding program. The new cultivar has a large sized white flower and a very compact plant habit that does not need cold temperatures to flower.

'AMOZ0002' originated from a sibling cross made in April 2011 in a controlled breeding environment in Enkhuizen, The Netherlands. The female parent was the proprietary plant designated 'P1401-5', unpatented, with white flowers, is earlier to flower and has smaller flowers.

The male parent of 'AMOZ0002' is not known. The seed was sown in September 2011 and 'AMOZ0002' was selected as one flowering plant within the progeny of the stated open pollination in March 2012 in a controlled environment in Enkhuizen, The Netherlands.

The first act of asexual reproduction of 'AMOZ0002' was accomplished when vegetative cuttings were propagated from the initial selection in March 2012 in a controlled environment in Enkhuizen, The Netherlands.

BRIEF SUMMARY OF INVENTION

Horticultural examination of plants grown from cuttings of the plant initiated in June 2012, and continuing thereafter, has demonstrated that the combination of characteristics as herein disclosed for 'AMOZ0002' are firmly fixed and are retained through successive generations of asexual reproduction.

'AMOZ0002' has not been observed under all possible environmental conditions. The phenotype may vary significantly with variations in environment such as temperature, light intensity and day length.

A Plant Breeder's Right for this cultivar was applied for in the European Union on Aug. 1, 2017, No. 2017/1899. 'AMOZ0002' has not been made publicly available prior to the effective filing date of this application, notwithstanding any disclosure that may have been made less than one year prior to the effective filing date of this application by the inventor or another who obtained 'AMOZ0002' directly from the inventor.

The following traits have been repeatedly observed and are determined to be basic characteristics of the new variety. The combination of these characteristics distinguishes this *Arenaria* as a new and distinct variety.

BRIEF DESCRIPTION OF THE PHOTOGRAPHS

The accompanying photographic drawings show typical flower and foliage characteristics of 'AMOZ0002' with colors being as true as possible with an illustration of this type.

Figure 1:
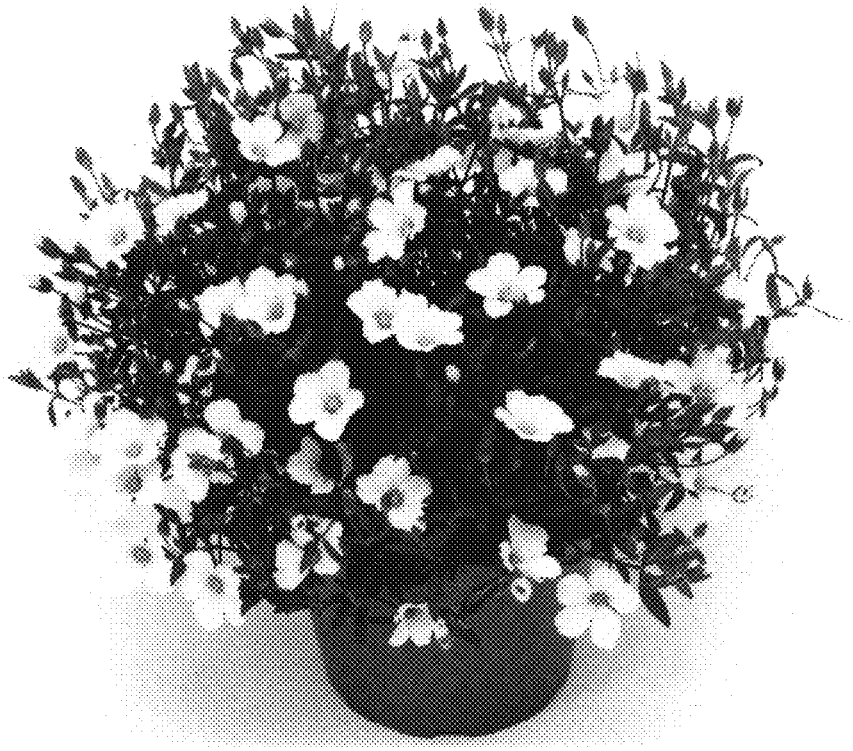
Figure 2:
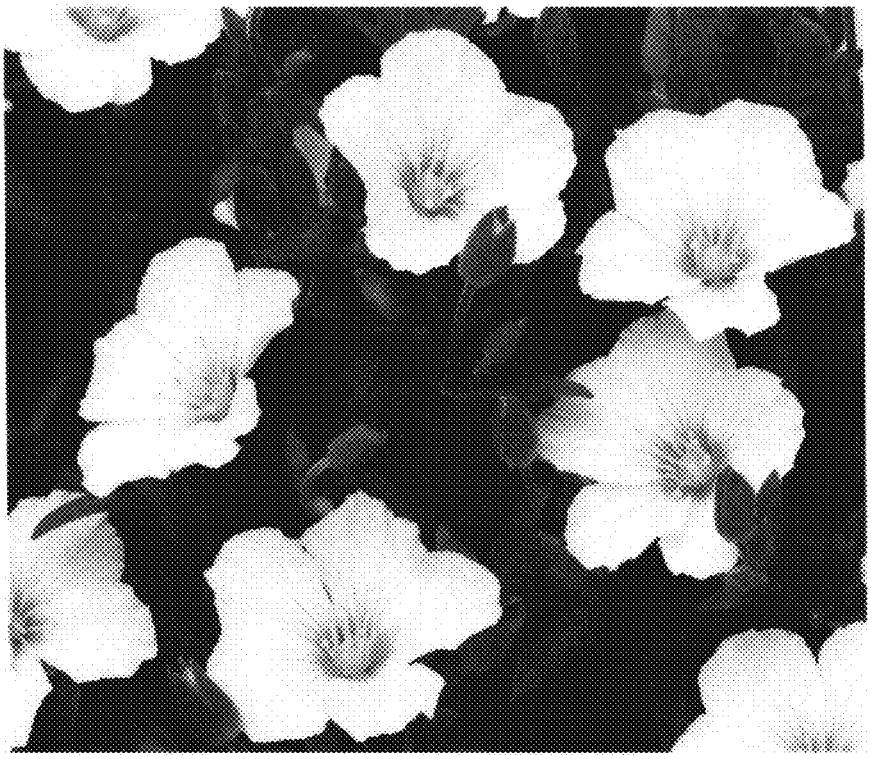

The photographic drawings show a flowering potted plant of the new variety in FIG. 1, and a close-up of the flowers in FIG. 2.

DETAILED BOTANICAL DESCRIPTION

The plant descriptions, measurements and aforementioned photographs were taken in Enkhuizen, The Netherlands, in a greenhouse under natural light in July 2016. These plants used for the photographs and descriptions were about 3 months old and were grown in an outdoor container trial.

Color references are made to The Royal Horticultural Society Colour Chart (R.H.S.) 2001.

TABLE 1

DIFFERENCES BETWEEN THE NEW VARIETY 'AMOZ0002' AND A SIMILAR VARIETY

| | 'AMOZ0002' | 'AMOZ0001' (U.S. Plant Pat. No. 23,842) |
|---|---|---|
| Flowing response: | Early | Very early |
| Flower size: | Smaller | Larger |
| Plant habit: | Compact | Vigorous |

Plant:
*Form, growth and habit*.—Compact and tightly mounded, freely branching, freely flowering.
*Plant height*.—9-10.5 cm.
*Plant height* (*inflorescence included*).—10-11 cm.
*Plant width*.—16-18 cm.
Roots:
*Number of days to initiate roots*.—About 12 days at about 18 degrees C.
*Number of days to produce a rooted cutting*.—3-4 weeks at 18 degrees C.
*Type*.—Fine, fibrous, free branching.
*Color*.—RHS N155B but whiter.
Foliage:
*Arrangement*.—Opposite.
*Attachment*.—Sessile.
*Immature, leaf color, upper surface*.—RHS 137C.
*Lower surface*.—RHS 144A.
*Mature, leaf color, upper surface*.—RHS 137C.
*Lower surface*.—RHS 144A.
*Length*.—0.6-1.2 cm.
*Width*.—0.3-0.4 cm.
*Shape*.—Lanceolate.
*Base shape*.—Shortly attenuate.
*Apex shape*.—Apiculate.
*Margin*.—Entire.
*Texture, upper surface*.—Smooth.
*Lower surface*.—Smooth.
*Color of veins, upper surface*.—RHS 137D.
*Color of veins, lower surface*.—RHS 144B but slightly darker.
*Venation pattern*.—Pinnate.
Stem:
*Color of stem*.—RHS 137D.
*Length of stem*.—2.5-3 cm.
*Diameter*.—0.2 cm.
*Length of internodes*.—0.4-0.6 cm.
*Texture*.—Smooth.
*Color of peduncle*.—RHS 137D.
*Length of peduncle*.—0.4-0.5 cm.
*Peduncle diameter*.—0.1-0.15 cm.
*Texture*.—Smooth.
Inflorescence:
*Type*.—Single, rotate, composed of 5 petals; flowers held above the plant.
*Quantity of inflorescences per plant*.—About 125.
*Quantity of inflorescences per lateral stem*.—1-6.
*Lastingness of individual blooms on the plant*.—About 1 week.
*Fragrance*.—None.
Bud (just before opening/showing color):
*Color*.—RHS 155D.
*Length*.—0.4-0.5 cm.
*Width*.—0.2-0.3 cm.
*Shape*.—Oblong.
Corolla:
Immature inflorescence:
*Diameter*.—1.4 cm.
*Color of petals, upper surface*.—RHS 155D but whiter.
*Lower surface*.—RHS 155D but lighter.
Mature inflorescence:
*Flower diameter*.—1.8 cm.
*Depth*.—1.3 cm.
*Petal color, upper surface*.—RHS 155D but whiter.
*Lower surface*.—RHS 155D but whiter.
*Length of petal*.—0.7-0.8 cm.
*Width of petal*.—0.5-0.6 cm.
*Shape*.—Spathulate.
*Apex shape*.—Rounded.
*Margin*.—Entire; and somewhat wavy.
*Petal texture, upper surface*.—Smooth.
*Lower surface*.—Smooth.
*Corolla texture, inside*.—Smooth.
*Outside*.—Smooth.
Calyx:
*Quantity*.—4.
*Color, upper surface*.—RHS 137B.
*Lower surface*.—RHS 137C.
*Length*.—0.3-0.4 cm.
*Width*.—0.1-0.3 cm.
*Shape*.—Oblong.
*Apex shape*.—Acute.
*Based*.—Fused.
*Margins*.—Entire.
*Texture, upper/inner surface*.—Smooth.
*Lower/outer surface*.—Stellate hairs.
Reproductive organs:
Gynoecium:
*Pistil quantity*.—1.
*Length*.—0.5 cm.
*Style color*.—RHS 143B.
*Style length*.—0.4 cm.
*Stigma color*.—RHS 143A.
*Stigma shape*.—Not observed.
*Ovary color*.—RHS 155B.
Androecioum:
*Stamens, quantity*.—12.
*Color of filaments*.—RHS 155C.
*Length filaments*.—1.0 cm.
*Anther color*.—RHS 18B.
*Anther length*.—0.1 cm.
*Anther shape*.—Ovate.
*Color of pollen*.—RHS 8B.
*Pollen amount*.—Abundant.
*Fertility/seed set*.—Has not been observed.
*Disease/pest resistance*.—Has not been observed.

What is claimed is:

1. A new and distinct variety of *Arenaria* plant named 'AMOZ0002' substantially as illustrated and described herein.

* * * * *